United States Patent [19]

Smith

[11] 4,168,383

[45] Sep. 18, 1979

[54] AMIDES OF 6-HYDROXY-PGE₁ COMPOUNDS

[75] Inventor: Herman W. Smith, Kalamazoo Township, Kalamazoo County, Mich.

[73] Assignee: The Upjohn Company, Kalamazoo, Mich.

[21] Appl. No.: 918,523

[22] Filed: Jun. 23, 1978

Related U.S. Application Data

[63] Continuation-in-part of Ser. No. 812,794, Jul. 5, 1977, Pat. No. 4,131,738.

[51] Int. Cl.² ................................................ C07C 177/00
[52] U.S. Cl. ......................... 544/176; 260/557 R; 260/559 R; 260/326.5 J; 260/239 BF; 260/239 B; 546/226; 560/121; 562/503; 544/386
[58] Field of Search .................. 560/53, 121; 544/176, 544/386; 260/557 R, 559 R, 239 BF, 239 B; 546/226; 562/503

Primary Examiner—Paul J. Killos
Attorney, Agent, or Firm—Robert A. Armitage

[57] ABSTRACT

The present invention provides amides of 6-hydroxy-PGE₁ compounds which are useful pharmacological agents. These analogs are useful as prostacyclin-like drugs.

47 Claims, No Drawings

AMIDES OF 6-HYDROXY-PGE₁ COMPOUNDS

CROSS REFERENCE TO RELATED APPLICATION

This application is a continuation-in-part of Ser. No. 812,794, filed July 5, 1977, now issued as U.S. Pat. No. 4,131,738.

The present invention relates to amides of 6-hydroxy-PGE₁ compounds, the preparation and use of which are described in U.S. Ser. No. 812,794, filed July 5, 1977, now issued as U.S. Pat. No. 4,131,738 on Dec. 26, 1978.

The essential material constituting a disclosure of the instant invention is incorporated by reference here from U.S. Pat. No. 4,131,738.

I claim:

1. A prostacyclin analog of the formula

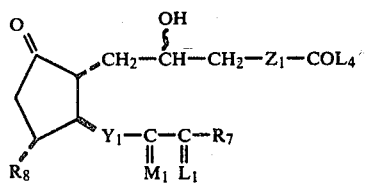

wherein $R_8$ is hydrogen, hydroxy, or hydroxymethyl;
wherein $Z_1$ is
 (1) $-(CH_2)_g-CH_2-CH_2-$,
 (2) $-(CH_2)_g-CH_2-CF_2-$, or
 (3) trans$-(CH_2)_g-CH=CH-$,
wherein g is the integer one 2 or 3;
wherein $Y_1$ is
 (1) trans$-CH=CH-$,
 (2) cis$-CH=CH-$,
 (3) $-CH_2CH_2-$,
 (4) trans$-CH=C(Hal)-$, or
 (5) $-C\equiv C-$,
wherein Hal is chloro or bromo;
wherein $M_1$ is

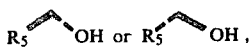

wherein $R_5$ is hydrogen or alkyl with one to 4 carbon atoms, inclusive;
wherein $L_1$ is

or a mixture of

and

wherein $R_3$ and $R_4$ are hydrogen, methyl, or fluoro, being the same or different, with the proviso that one of $R_3$ and $R_4$ is fluoro only when the other is hydrogen or fluoro;
wherein $L_4$ is
 (a) amino of the formula $-NR_{21}R_{22}$, wherein $R_{21}$ and $R_{22}$ are hydrogen; alkyl of one to 12 carbon atoms, inclusive; cycloalkyl of 3 to 10 carbon atoms, inclusive; aralkyl of 7 to 12 carbon atoms, inclusive; phenyl; phenyl substituted with one, 2, or 3 chloro, alkyl of one to 3 carbon atoms, inclusive; hydroxy; carboxy, alkoxycarbonyl of one to 4 carbon atoms, inclusive; or nitro; carboxyalkyl of one to 4 carbon atoms, inclusive; carbamoylalkyl of one to 4 carbon atoms, inclusive; cyanoalkyl of one to 4 carbon atoms, inclusive; acetylalkyl of one to 4 carbon atoms, inclusive; benzoylalkyl of one to 4 carbon atoms, inclusive; benzoylalkyl substituted by one, 2, or 3 chloro, alkyl of one to 3 carbon atoms, inclusive; hydroxy, alkoxy of one to 3 carbon atoms, inclusive; carboxy, alkoxycarbonyl of one to 4 carbon atoms, inclusive; or nitro; pyridyl; pyridyl substituted by one, 2, or 3 chloro, alkyl of one to 3 carbon atoms, inclusive; or alkoxy of one to 3 carbon atoms, inclusive; pyridylalkyl of one to 4 carbon atoms, inclusive; pyridylalkyl of one to 4 carbon atoms, inclusive; pyridylalkyl substituted by one, 2, or 3 chloro, alkyl of one to 3 carbon atoms, inclusive; hydroxy, alkoxy of one to 3 carbon atoms, inclusive; hydroxyalkyl of one to 4 carbon atoms, inclusive; dihydroxyalkyl of one to 4 carbon atoms, and trihydroxyalkyl of one to 4 carbon atoms; with the further proviso that not more than one of $R_{21}$ and $R_{22}$ is other than hydrogen or alkyl;
 (b) cycloamino selected from the group consisting of

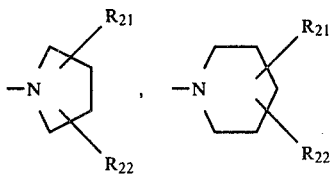

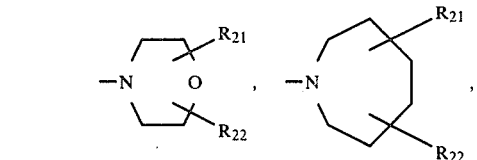

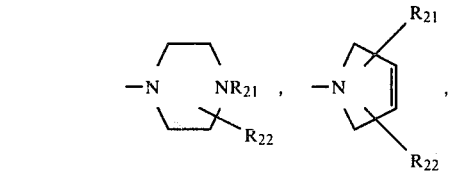

or 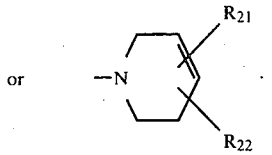

wherein $R_{21}$ and $R_{22}$ are as defined above;
(c) carbonylamino of the formula $-NR_{23}COR_{21}$, wherein $R_{23}$ is hydrogen or alkyl of one to 4 carbon atoms and $R_{21}$ is as defined above;
(d) sulfonylamino of the formula $-NR_{23}SO_2R_{21}$, wherein $R_{21}$ and $R_{23}$ are as defined above; or
(e) hydrazino of the formula $-NR_{23}R_{24}$, wherein $R_{24}$ is amino of the formula $-NR_{21}R_{22}$, as defined above, or cycloamino, as defined above;

wherein $R_7$ is
(1) $-(CH_2)_m-CH_3$,

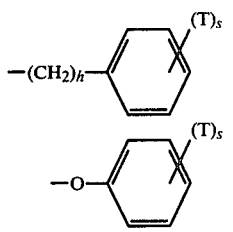

wherein m is the integer one to 5, inclusive, h is the integer zero to 3, inclusive; s is the integer zero, one, 2, or 3, and T is chloro, fluoro, trifluoromethyl, alkyl of one to 3 carbon atoms, inclusive, or alkoxy of one to 3 carbon atoms, inclusive, or with the proviso that not more than two T's are other than alkyl.

2. A prostacyclin analog according to claim 1, wherein $R_8$ is hydroxymethyl.

3. 11-Deoxy-11α-hydroxymethyl-6-hydroxy-PGE$_1$, amide, a prostacyclin analog according to claim 2.

4. A prostacyclin analog according to claim 1, wherein $R_8$ is hydrogen.

5. 11-Deoxy-6-hydroxy-PGE$_1$, amide, a prostacyclin analog according to claim 4.

6. A prostacyclin analog according to claim 1, wherein $R_8$ is hydroxy.

7. A prostacyclin analog according to claim 6, wherein ~OH is beta.

8. 6β-Hydroxy-PGE$_1$, amide, a prostacyclin analog according to claim 7.

9. A prostacyclin analog according to claim 6, wherein ~OH is alpha.

10. 6α-Hydroxy-PGE$_1$, amide, a prostacyclin analog according to claim 9.

11. 6α-Hydroxy-15-methyl-PGE$_1$, amide, a prostacyclin analog according to claim 9.

12. 6α-Hydroxy-16,16-dimethyl-PGE$_1$, amide, a prostacyclin analog according to claim 9.

13. 6α-Hydroxy-16,16-difluoro-PGE$_1$, amide, a prostacyclin analog according to claim 9.

14. A prostacyclin analog according to claim 6, wherein ~OH is a mixture of α-OH and β-OH.

15. A prostacyclin analog according to claim 14, wherein $Y_1$ is cis—CH=CH—.

16. 6-Hydroxy-cis-13-PGE$_1$, amide, a prostacyclin analog according to claim 15.

17. A prostacyclin analog according to claim 14, wherein $Y_1$ is —C≡C—.

18. 6-Hydroxy-13,14-dide-ydro-PGE$_1$, amide, a prostacyclin analog according to claim 17.

19. A prostacyclin analog according to claim 14, wherein $Y_1$ is trans—CH=C(Hal)—.

20. 6-Hydroxy-14-chloro-PGE$_1$, amide, a prostacyclin analog according to claim 19.

21. A prostacyclin analog according to claim 14, wherein $Y_1$ is —CH$_2$CH$_2$—.

22. 6-Hydroxy-13,14-dihydro-PGE$_1$, amide, a prostacyclin analog according to claim 21.

23. A prostacyclin analog according to claim 14, wherein $Y_1$ is trans—CH=CH—.

24. A prostacyclin analog according to claim 23, wherein $Z_1$ is —(CH$_2$)$_g$—CH$_2$—CF$_2$—.

25. 2,2-Difluoro-6-hydroxy-15-methyl-PGE$_1$, amide, a prostacyclin analog according to claim 24.

26. A prostacyclin analog according to claim 23, wherein $Z_1$ is trans—(CH$_2$)$_g$—CH=CH—.

27. trans-2,3-Didehydro-6-hydroxy-PGE$_1$, amide, a prostacyclin analog according to claim 26.

28. A prostacyclin analog according to claim 23, wherein $Z_1$ is —(CH$_2$)$_g$—CH$_2$—CH$_2$—.

29. A prostacyclin analog according to claim 28, wherein g is one.

30. A prostacyclin analog according to claim 29, wherein $R_7$ is 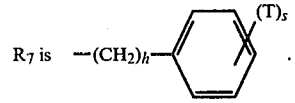.

31. 6-Hydroxy-17-phenyl-18,19,20-trinor-PGE$_1$, amide, a prostacyclin analog according to claim 30.

32. A prostacyclin analog according to claim 29, wherein $R_7$ is 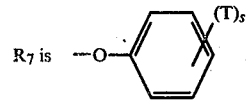.

33. 6-Hydroxy-16-phenoxy-17,18,19,20-tetranor-PGE$_1$, amide, a prostacyclin analog according to claim 32.

34. A prostacyclin analog according to claim 29, wherein $R_7$ is —(CH$_2$)$_m$—CH$_3$—.

35. A prostacyclin analog according to claim 34, wherein m is 3.

36. A prostacyclin analog according to claim 35, wherein $R_5$ is methyl.

37. 6-Hydroxy-15-methyl-PGE$_1$, amide, a prostacyclin analog according to claim 36.

38. A prostacyclin analog according to claim 35, wherein $R_5$ is hydrogen.

39. A prostacyclin analog according to claim 38, wherein at least one of $R_3$ and $R_4$ is fluoro.

40. 6-Hydroxy-16,16-difluoro-PGE$_1$, amide, a prostacyclin analog according to claim 39.

41. A prostacyclin analog according to claim 38, wherein at least one of $R_3$ and $R_4$ is methyl.

42. 6-Hydroxy-16,16-dimethyl-PGE$_1$, amide, a prostacyclin analog according to claim 41.

43. A prostacyclin analog according to claim 38, wherein $R_3$ and $R_4$ are both hydrogen.

44. 6-Hydroxy-PGE$_1$, piperadyl amide, a prostacyclin analog according to claim 43.

45. 6-Hydroxy-PGE$_1$, methylsulfonyl amide, a prostacyclin analog according to claim 43.

46. 6-Hydroxy-PGE$_1$, pyridyl amide, a prostacyclin analog according to claim 43.

47. 6-Hydroxy-PGE$_1$, amide, a prostacyclin analog according to claim 43.

* * * * *